US012633009B2

(12) United States Patent
Tsunomori et al.

(10) Patent No.: US 12,633,009 B2
(45) Date of Patent: May 19, 2026

(54) IMAGE PROCESSING APPARATUS, IMAGE PROCESSING SYSTEM AND STORAGE MEDIUM

(71) Applicant: Konica Minolta, Inc., Tokyo (JP)

(72) Inventors: Akinori Tsunomori, Kodaira (JP); Ryoichi Watanabe, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 50 days.

(21) Appl. No.: 18/181,651

(22) Filed: Mar. 10, 2023

(65) Prior Publication Data

US 2023/0290023 A1 Sep. 14, 2023

(30) Foreign Application Priority Data

Mar. 14, 2022 (JP) ................................. 2022-038889

(51) Int. Cl.
| | |
|---|---|
| *G06T 11/26* | (2026.01) |
| *A61B 5/11* | (2006.01) |
| *G06T 7/00* | (2017.01) |
| *G16H 30/20* | (2018.01) |
| *G16H 50/30* | (2018.01) |

(52) U.S. Cl.
CPC ............ *G06T 11/26* (2026.01); *A61B 5/1107* (2013.01); *G06T 7/0012* (2013.01); *G16H 30/20* (2018.01); *G16H 50/30* (2018.01); *G06T 2207/30061* (2013.01)

(58) Field of Classification Search
CPC ................. G06T 11/206; G06T 7/0012; G06T 2207/30061; G16H 50/30
See application file for complete search history.

(56) References Cited

U.S. PATENT DOCUMENTS

| | | | | |
|---|---|---|---|---|
| 12,288,606 | B2 * | 4/2025 | Sugiyama | ............. G06T 19/006 |
| 2013/0131465 | A1 * | 5/2013 | Yamamoto | ........... A61B 5/7271 |
| | | | | 600/300 |
| 2013/0268622 | A1 * | 10/2013 | Tomono | ............. G06Q 30/0601 |
| | | | | 709/217 |
| 2022/0327423 | A1 * | 10/2022 | Tsuzuki | ................. G06N 20/00 |

(Continued)

FOREIGN PATENT DOCUMENTS

| | | |
|---|---|---|
| CN | 110198672 A | 9/2019 |
| JP | 2012-45373 A | 3/2012 |
| JP | 2019-063328 A | 4/2019 |

(Continued)

OTHER PUBLICATIONS

Office Action issued for the related Chinese patent application No. 202310255185.X, dated Jul. 10, 2025, with its English translation, 21 pages.

(Continued)

*Primary Examiner* — Grace Q Li
(74) *Attorney, Agent, or Firm* — LUCAS & MERCANTI, LLP

(57) ABSTRACT

An image processing apparatus includes a hardware processor. The hardware processor obtains a medical image in which a subject is imaged, calculates a value of an evaluation item based on the medical image, sets evaluation items among a plurality of evaluation items, generates a radar chart using the value of each of the set evaluation items, and outputs the radar chart.

16 Claims, 11 Drawing Sheets

(56) References Cited

U.S. PATENT DOCUMENTS

| | | | | |
|---|---|---|---|---|
| 2023/0238118 A1* | 7/2023 | Nakamura | ............. | G16H 15/00 705/2 |
| 2024/0008675 A1* | 1/2024 | Torizu | ................... | A47J 31/002 |

FOREIGN PATENT DOCUMENTS

| | | | |
|---|---|---|---|
| JP | 2019-118820 | A | 7/2019 |
| JP | 2019-122449 | A | 7/2019 |
| JP | 2020-171427 | A | 10/2020 |

OTHER PUBLICATIONS

Office Action issued for the related Japanese patent application No. 2022-038889, dated Aug. 5, 2025, with its English translation, 6 pages.

Office Action, dated Dec. 29, 2025, which was issued for the corresponding Chinese Patent Application No. CN 202310255185. X, 25 pages, with English translation.

* cited by examiner

FIG.3

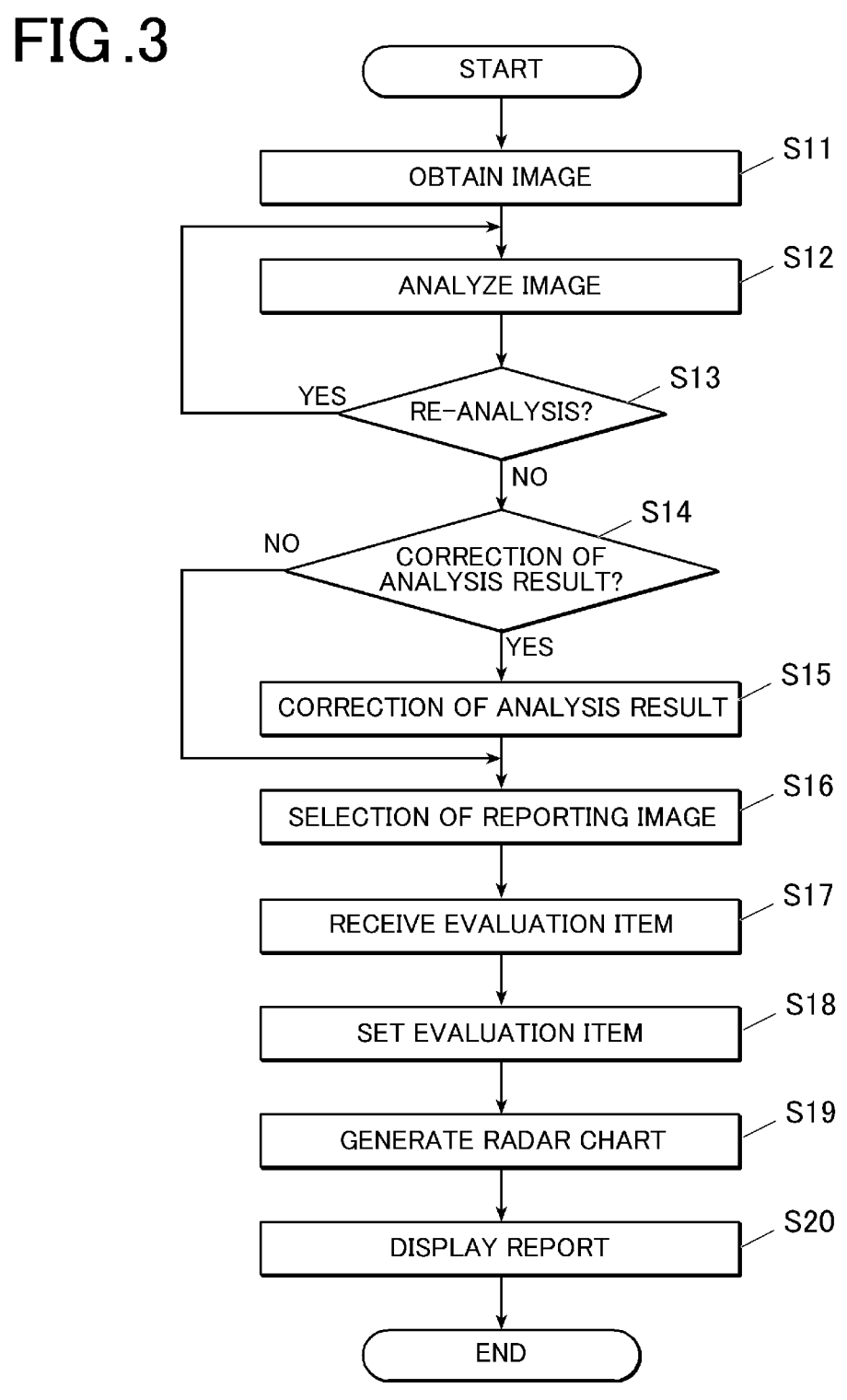

```
                    ( START )
                        │
                        ▼
              ┌──────────────────┐
              │   OBTAIN IMAGE   │ ─── S11
              └──────────────────┘
                        │
         ┌──────────────▼──────────────┐
         │                             │
         │    ┌──────────────────┐     │
         │    │  ANALYZE IMAGE   │ ─── S12
         │    └──────────────────┘
         │              │
         │              ▼
         │          ╱───────────╲      S13
    YES  │         ╱ RE-ANALYSIS? ╲
         └────────╲               ╱
                   ╲─────────────╱
                        │ NO
                        ▼
                    ╱───────────────╲   S14
              NO   ╱  CORRECTION OF   ╲
         ┌───────╲ ANALYSIS RESULT?  ╱
         │        ╲                 ╱
         │         ╲───────────────╱
         │              │ YES
         │              ▼
         │    ┌──────────────────────────┐
         │    │ CORRECTION OF ANALYSIS RESULT │ ─── S15
         │    └──────────────────────────┘
         │              │
         └──────────────▼
              ┌──────────────────────────┐
              │ SELECTION OF REPORTING IMAGE │ ─── S16
              └──────────────────────────┘
                        │
                        ▼
              ┌──────────────────────────┐
              │  RECEIVE EVALUATION ITEM  │ ─── S17
              └──────────────────────────┘
                        │
                        ▼
              ┌──────────────────────────┐
              │    SET EVALUATION ITEM    │ ─── S18
              └──────────────────────────┘
                        │
                        ▼
              ┌──────────────────────────┐
              │   GENERATE RADAR CHART    │ ─── S19
              └──────────────────────────┘
                        │
                        ▼
              ┌──────────────────────────┐
              │      DISPLAY REPORT       │ ─── S20
              └──────────────────────────┘
                        │
                        ▼
                    (  END  )
```

| IMAGE ANALYSIS PROGRAM Ver1.0 | IMAGE ANALYSIS PROGRAM Ver2.0 |
|---|---|

MEASURABLE ITEMS

MAXIMUM LUNG FIELD AREA
MINIMUM LUNG FIELD AREA
CHANGE IN LUNG FIELD AREA
ESTIMATED MAXIMUM VOLUME
ESTIMATED MINIMUM VOLUME
DIAPHRAGM DISPLACEMENT(R)
DIAPHRAGM DISPLACEMENT(L)

MEASURABLE ITEMS

MAXIMUM LUNG FIELD AREA
MINIMUM LUNG FIELD AREA
CHANGE IN LUNG FIELD AREA
ESTIMATED MAXIMUM VOLUME
ESTIMATED MINIMUM VOLUME
DIAPHRAGM DISPLACEMENT(R)
DIAPHRAGM DISPLACEMENT(L)
NARROWING OF TRACHEAL DIAMETER

FIG.11

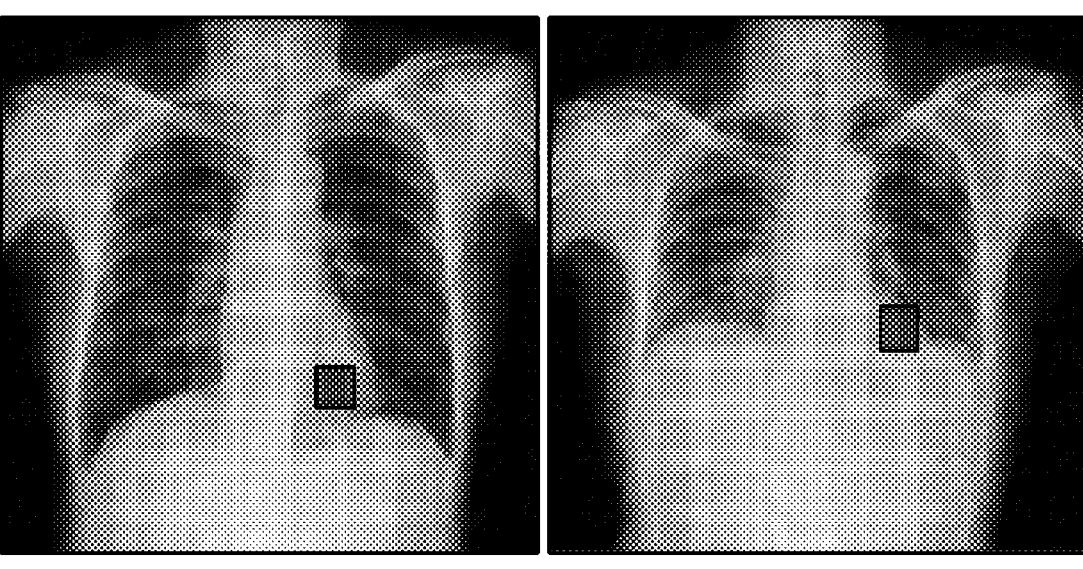

IMAGE PROCESSING APPARATUS, IMAGE PROCESSING SYSTEM AND STORAGE MEDIUM

REFERENCE TO RELATED APPLICATIONS

The entire disclosure of Japanese Patent Application No. 2022-038889, filed on Mar. 14, 2022, including description, claims, drawings and abstract is incorporated herein by reference in its entirety.

TECHNICAL FIELD

The present disclosure relates to an image processing apparatus, an image processing system and a storage medium.

DESCRIPTION OF THE RELATED ART

There has been a technique of analyzing an X-ray image(s) and obtaining a parameter (feature amount) for a disease, respiratory function or the like, and a doctor or another makes an evaluation (diagnoses a disease, grasp information on respiratory function, etc.) by checking whether the result shows a tendency similar to that of the disease, the respiratory function or the like. In particular, in dynamic analysis using a dynamic image obtained by dynamic imaging, time-series information can be obtained as a parameter and its tendency can be checked.

Since the interior of the body is intricately controlled and it is difficult to make an evaluation thereon using one parameter only, it has been proposed to display a radar chart with a plurality of parameters. (See, for example, JP 2019-63328 A.)

SUMMARY OF THE INVENTION

However, observation sites and diseases have different features. Hence, a radar chart with fixed parameters disclosed in JP 2019-63328 A cannot be used widely in medical practice.

Objects of the present disclosure include providing an image processing apparatus, an image processing system and a storage medium storing a program capable of generating a suitable radar chart(s) in accordance with a disease and an observation site about which analysis is performed.

To achieve at least one of the abovementioned objects, according to a first aspect of the present disclosure, there is provided an image processing apparatus including a hardware processor that obtains a medical image in which a subject is imaged, calculates a value of an evaluation item based on the medical image, sets evaluation items among a plurality of evaluation items, generates a radar chart using the value of each of the set evaluation items, and outputs the radar chart.

To achieve at least one of the abovementioned objects, according to a second aspect of the present disclosure, there is provided an image processing system including:

an examination apparatus that obtains a medical image in which a subject is imaged;

an image processing apparatus that is connected to the examination apparatus; and a hardware processor that obtains the medical image from the examination apparatus, calculates a value of an evaluation item based on the medical image, sets evaluation items among a plurality of evaluation items, generates a radar chart using the value of each of the set evaluation items, and outputs the radar chart.

To achieve at least one of the abovementioned objects, according to a third aspect of the present disclosure, there is provided a non-transitory computer-readable storage medium storing a program that causes a computer of an image processing apparatus to:

obtain a medical image in which a subject is imaged;

calculate a value of an evaluation item based on the medical image;

set evaluation items among a plurality of evaluation items;

generate a radar chart using the value of each of the set evaluation items; and output the radar chart.

BRIEF DESCRIPTION OF THE DRAWINGS

The advantages and features provided by one or more embodiments of the present disclosure will become more fully understood from the detailed description given hereinafter and the appended drawings, which are given by way of illustration only, and thus are not intended as a definition of the limits of the present disclosure, wherein:

FIG. 3 is a flowchart showing a report creation process;

FIG. 5 shows an example of a measurement result display screen;

FIG. 10 shows image analysis programs and measurable items (radar chart items) with the programs;

FIG. 11 shows an example (examples of frame images) of a dynamic image with a heart ROI as a region to be analyzed (analysis region);

DETAILED DESCRIPTION

Hereinafter, one or more embodiments of the present disclosure will be described in detail with reference to the drawings. However, the scope of the present disclosure is not limited to the embodiments or illustrated examples.

<Configuration of Image Processing System 100>

First, configuration of an image processing system according to an embodiment(s) will be described.

Figure 1:
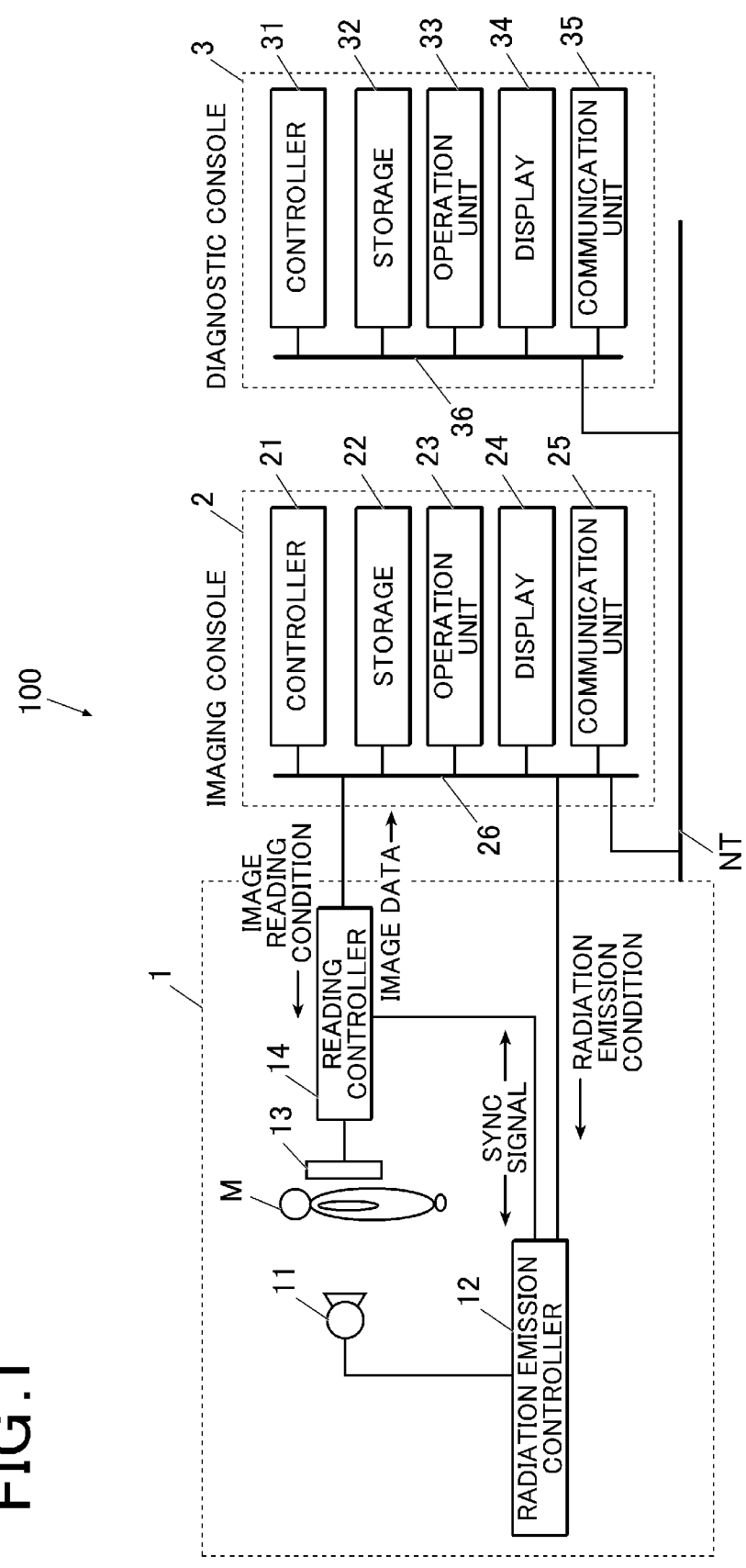
FIG. 1 shows the overall configuration of an image processing system according to an embodiment(s) of the present disclosure.

FIG. 1 shows the overall configuration of an image processing system 100 according to an embodiment(s).

As shown in FIG. 1, the image processing system 100 includes an imaging apparatus 1, an imaging console 2 connected with the imaging apparatus 1 via a communication cable or the like, and a diagnostic console 3 connected with the imaging console 2 via a communication network NT, such as a LAN (Local Area Network). These apparatuses of the image processing system 100 are in conformity with DICOM (Digital Image and Communications in Medicine) standard and communicate with one another in conformity with DICOM. The imaging apparatus 1 and the imaging console 2 constitute an examination apparatus of this embodiment.

<Configuration of Imaging Apparatus 1>

The imaging apparatus 1 is an imager that images/photographs a dynamic state (dynamic imaging) of a living body. Examples of the dynamic state include change in shape of lungs, namely expansion and contraction of lungs, with respiration, and pulsation of a heart. Dynamic imaging is performed by repeatedly emitting pulsed radiation, such as X-rays, to a subject at intervals of a predetermined time (pulse emission) or continuously emitting radiation without a break to a subject at a low dose rate (continuous emission), thereby generating a plurality of images showing the dynamic state of a subject. A series of images obtained by dynamic imaging is called a dynamic image (medical image). Images constituting a dynamic image are called frame images. Dynamic images include moving images, but do not include images obtained by performing still imaging while displaying a moving image. In the embodiment(s) described below, dynamic imaging of a chest is performed by pulse emission as an example.

A radiation source 11 is arranged so as to face a radiation detector 13 with a subject M (examinee) in between, and emits radiation (X-rays) to the subject M under the control of a radiation emission controller 12.

The radiation emission controller 12 is connected with the imaging console 2, and controls the radiation source 11 on the basis of radiation emission conditions input from the imaging console 2 to perform radiographing (radiographic imaging or imaging with radiation). The radiation emission conditions input from the imaging console 2 include a pulse rate, a pulse width, a pulse interval, the number of frame images to be taken by one dynamic imaging, a value of current of an X-ray tube, a value of voltage of the X-ray tube, and a type of an added filter. The pulse rate is the number of times that radiation is emitted per second, and matches a frame rate described below. The pulse width is a period of time (duration) of one radiation emission. The pulse interval is a period of time from start of one radiation emission to start of the next radiation emission, and matches a frame interval described below.

The radiation detector 13 is constituted of a semiconductor image sensor, such as an FPD (Flat Panel Detector). The FPD is constituted of detection elements (pixels) arranged at predetermined points on a substrate, such as a glass substrate, in a matrix. The detection elements detect radiation (intensity of radiation) that has been emitted from the radiation source 11 and passed through at least the subject M, convert the detected radiation into electric signals, and accumulate the electric signals therein. The pixels are provided with switching elements, such as TFTs (Thin Film Transistors). There are an indirect conversion FPD that converts X-rays into electric signals with photoelectric conversion element(s) via scintillator(s) and a direct conversion FPD that directly converts X-rays into electric signals. Either of these can be used.

The radiation detector 13 is arranged so as to face the radiation source 11 with the subject M in between.

A reading controller 14 is connected with the imaging console 2. The reading controller 14 controls the switching elements of the pixels of the radiation detector 13 on the basis of image reading conditions input from the imaging console 2 to switch (change) the pixels from which the accumulated electric signals are read, thereby reading the electric signals accumulated in the radiation detector 13 and obtaining image data. This image data is a frame image(s). Signal values of pixels of each frame image indicate density values. The reading controller 14 outputs the obtained frame images to the imaging console 2. The image reading conditions include a frame rate, a frame interval, a pixel size, and an image size (matrix size). The frame rate is the number of frame images that are obtained per second, and matches the pulse rate described above. The frame interval is a period of time from start of one frame image obtainment to start of the next frame image obtainment, and matches the pulse interval described above.

The radiation emission controller 12 and the reading controller 14 are connected with one another, and exchange sync signals to synchronize radiation emission and image reading with one another.

<Configuration of Imaging Console 2>

The imaging console 2 outputs the radiation emission conditions and the image reading conditions to the imaging apparatus 1 to control radiographing and radiograph reading that are performed by the imaging apparatus 1, and also displays dynamic images obtained (generated) by the imaging apparatus 1 so that a radiographer (user), such as a radiologist, can check if positioning has no problem, and also can determine if the dynamic images are suitable for diagnosis.

The imaging console 2 includes, as shown in FIG. 1, a controller 21, a storage 22, an operation unit 23, a display 24 and a communication unit 25. These components are connected with one another via a bus 26.

The controller 21 includes a CPU (Central Processing Unit) and a RAM (Random Access Memory). The CPU of the controller 21 reads a system program(s) and various process programs stored in the storage 22 in response to the radiographer operating the operation unit 23, loads the read programs into the RAM, and performs various processes, such as an imaging control process described below, in accordance with the loaded programs, thereby performing centralized control of operation of each component of the imaging console 2 as well as radiation emission and image reading of the imaging apparatus 1.

The storage 22 is constituted of a nonvolatile semiconductor memory, a hard disk and/or the like. The storage 22 stores, for example, various programs to be executed by the controller 21, parameters necessary to perform processes of the programs, and data, such as process results. For example, the storage 22 stores a program for the imaging control process shown in FIG. 2. The storage 22 also stores the radiation emission conditions and the image reading conditions associated with respective examination target sites (in this embodiment, chest). The programs are stored in the form of a computer readable program code(s), and the controller 21 operates in accordance with the program code.

The operation unit 23 includes a keyboard including cursor keys, number input keys and various function keys, and a pointing device, such as a mouse, and outputs, to the controller 21, command signals input by the radiographer operating the keys of the keyboard or the mouse. The operation unit 23 may have a touchscreen on the display screen of the display 24. In this case, the operation unit 23 outputs command signals input via the touchscreen to the controller 21.

The display 24 is constituted of a monitor, such as an LCD (Liquid Crystal Display) or a CRT (Cathode Ray Tube), and displays commands input from the operation unit 23, data and so forth in accordance with commands of display signals input from the controller 21.

The communication unit 25 includes a LAN adapter, a modem and a TA (Terminal Adapter), and controls transmission and reception of data to and from apparatuses connected to the communication network NT.

<Configuration of Diagnostic Console 3>

The diagnostic control 3 is a dynamic image processing apparatus that obtains dynamic images from the imaging console 2, performs image processing on the obtained dynamic images, displays the dynamic images, and calculates feature amounts (parameters) on the basis of the dynamic images.

The diagnostic console 3 includes, as shown in FIG. 1, a controller 31 (hardware processor), a storage 32, an operation unit 33 (operation receiver), a display 34 and a communication unit 35. These components are connected with one another via a bus 36.

The controller 31 includes a CPU and a RAM. The CPU of the controller 31 reads a system program(s) and various process programs stored in the storage 32 in response to a user (e.g., radiographer/radiologist) operating the operation unit 33, loads the read programs into the RAM, and performs various processes, such as a report creation process described below, in accordance with the loaded programs, thereby performing centralized control of operation of each component of the diagnostic console 3.

The storage 32 is constituted of a nonvolatile semiconductor memory, a hard disk and/or the like. The storage 32 stores, for example, various programs for various processes, including a program for the report creation process shown in FIG. 3, to be executed by the controller 31, parameters necessary to perform the processes of the programs, and data, such as process results. The programs are stored in the form of a computer readable program code(s), and the controller 31 operates in accordance with the program code.

The storage 32 also stores dynamic images obtained in the past each associated with an image ID, patient (examinee) information (e.g., patient (examinee) ID, name, height, weight, age, sex, etc.), examination information (e.g., examination ID, examination date, examination target site (in this embodiment, chest), respiratory state, etc.) and so forth.

The operation unit 33 includes a keyboard including cursor keys, number input keys and various function keys, and a pointing device, such as a mouse, and outputs, to the controller 31, command signals input by the user operating the keys of the keyboard or the mouse. The operation unit 33 may have a touchscreen on the display screen of the display 34. In this case, the operation unit 33 outputs command signals input via the touchscreen to the controller 31.

The display 34 is constituted of a monitor, such as an LCD or a CRT, and performs various types of display in accordance with commands of display signals input from the controller 31.

The communication unit 35 includes a LAN adapter, a modem and a TA, and controls transmission and reception of data to and from apparatuses connected to the communication network NT.

<Operation of Image Processing System 100>

Next, operation of the image processing system 100 according to this embodiment will be described.

<Operation of Imaging Apparatus 1 and Imaging Console 2>

First, imaging that is performed by the imaging apparatus 1 and the imaging console 2 will be described.

Figure 2:
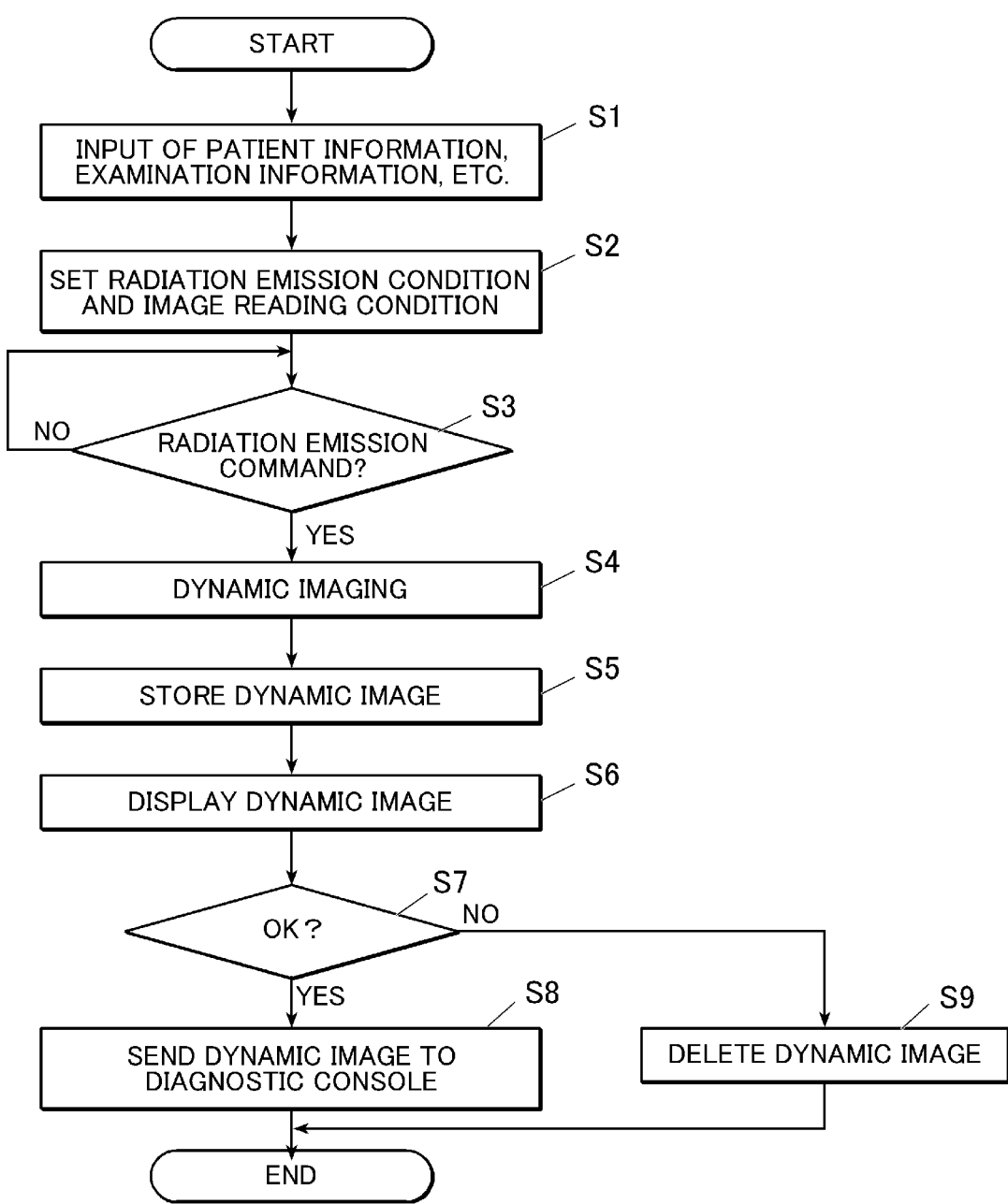
FIG. 2 is a flowchart showing an imaging control process.

FIG. 2 shows the imaging control process that is performed by the controller 21 of the imaging console 2. The imaging control process is performed by the controller 21 in cooperation with the program stored in the storage 22.

First, a radiographer (radiologist) operates the operation unit 23 of the imaging console 2 to input patient information on an examinee (subject M) and examination information (Step S1). Patient information and examination information are collectively called order information.

Next, the controller 21 reads radiation emission conditions from the storage 22 to set them in the radiation emission controller 12, and also reads image reading conditions from the storage 22 to set them in the reading controller 14 (Step S2).

Next, the controller 21 waits for a radiation emission command to be input by the radiographer operating the operation unit 23 (Step S3). The radiographer places the examinee (subject M) between the radiation source 11 and the radiation detector 13 and performs positioning. Also, the radiographer instructs the examinee (subject M) about the respiratory state (e.g., quiet breathing). When preparations for imaging are complete, the radiographer operates the operation unit 23 to input a radiation emission command.

When receiving the radiation emission command input through the operation unit 23 (Step S3; YES), the controller 21 outputs an imaging start command to the radiation emission controller 12 and the reading controller 14 to start dynamic imaging (Step S4). That is, the radiation source 11 emits radiation at pulse intervals set in the radiation emission controller 12, and the radiation detector 13 obtains (generates) a series of frame images accordingly.

When dynamic imaging for a predetermined number of frame images finishes, the controller 21 outputs an imaging end command to the radiation emission controller 12 and the reading controller 14 to stop dynamic imaging. The (predetermined) number of frame images to be taken covers at least one cycle of respiration.

The frame images obtained by dynamic imaging are successively input to the imaging console 2 and stored in the storage 22 associated with respective numbers (frame numbers) indicating what number in the imaging order the respective frame images have been taken (Step S5) and also displayed on the display 24 (Step S6). The radiographer checks the positioning or the like with the displayed dynamic image, and determines whether the dynamic image obtained by dynamic imaging is suitable for diagnosis (Imaging OK) or re-imaging is necessary (Imaging NG). Then, the radiographer operates the operation unit 23 to input the determination result.

If the radiographer inputs the determination result "Imaging OK" by operating the operation unit 23 (Step S7; YES), the controller 21 attaches, to the respective frame images obtained by dynamic imaging (e.g. writes, in the header region of the image data in DICOM), the image ID, with which the dynamic image is identified, the patient information, the examination information, the radiation emission conditions, the image reading conditions, the respective numbers (frame numbers) indicating what number in the imaging order the respective frame images have been taken and other information, and sends same to the diagnostic console 3 through the communication unit 25 (Step S8), and then ends the imaging control process. If the radiographer inputs the determination result "Imaging NG" by operating the operation unit 23 (Step S7; NO), the controller 21 deletes (the series of) the frame images from the storage 22 (Step S9), and then ends the imaging control process. In this case, re-imaging is necessary.

<Operation of Diagnostic Console 3>

Next, analysis of a dynamic image by the diagnostic console 3 will be described.

The diagnostic console 3 performs the report creation process shown in FIG. 3 with the controller 31 and the program stored in the storage 32 working together. Hereinafter, the report creation process will be described with reference to FIG. 3.

In the diagnostic console 3, the controller 31 receives (obtains) a series of frame images of a dynamic image from the imaging console 2 via the communication unit 35 (Step S11). The controller 31 stores, in the storage 32, the received series of frame images of a dynamic image associated with the image ID, the patient information, the examination information and so forth.

The controller 31 analyzes the dynamic image when the dynamic image is selected from among dynamic images stored in the storage 32 and a report creation command is made by a radiographer (user) operating the operation unit 33 (Step S12). More specifically, the controller 31 extracts an analysis region(s) to analyze and calculates feature amounts (parameter values).

In this embodiment, the controller 31 extracts lung field regions as the analysis region, and calculates values of the area of lung fields, displacement of diaphragm and so forth as the feature amounts (parameter values).

Next, the radiographer checks the analysis result obtained in Step S12, and the controller 31 receives, from the radiographer via the operation unit 33, a notification (Step S13) that re-analysis is necessary (Step S13; YES) or that re-analysis is unnecessary (Step S13; NO). If the controller 31 receives the notification that re-analysis is unnecessary (Step S13; NO), the process proceeds to Step S14. If the controller 31 receives the notification that re-analysis is necessary (Step S13; YES), the process returns to Step S12 in which the controller 31 re-analyzes the dynamic image.

The analysis result includes, for example, frames (e.g., "a" shown in FIG. 5, etc.) indicating lung fields in a lung field image. If frames indicating lung fields do not correctly enclose the lung fields, the radiographer makes the notification that re-analysis is necessary (Step S13; YES) using the operation unit 33.

If Step S13 is "NO", the radiographer determines whether the analysis result of the analysis in Step S12 needs to be corrected, and the controller 31 receives, from the radiographer via the operation unit 33, a notification (Step S14) that correction of the analysis result is unnecessary (Step S14; NO) or that correction of the analysis result is necessary (Step S14; YES). If the controller 31 receives the notification that correction of the analysis result is unnecessary (Step S14; NO), the process proceeds to Step S16. If the controller 31 receives the notification that correction of the analysis result is necessary (Step S14; YES), the process proceeds to Step S15 in which the radiographer corrects the analysis result.

If Step S14 is "YES", the radiographer corrects the analysis result of the analysis in Step S12, and the controller 31 receives the corrected analysis result from the radiographer via the operation unit 33 (Step S15). The analysis result may be corrected, for example, to delete parts (e.g., useless substances/objects or the like appearing in the medical image) undesirable to be displayed in a report to be created.

A setting may be made such that when the radiographer corrects a part in one frame image, the controller 31 corrects the same part in the other frame images.

Next, the radiographer selects an image(s) (frame image(s)) to display in a report to create (reporting image(s)), and the controller 31 receives the selected reporting image from the radiographer via the operation unit 33 (Step S16). For example, a lung field image(s) is selected as the reporting image.

Figure 4:
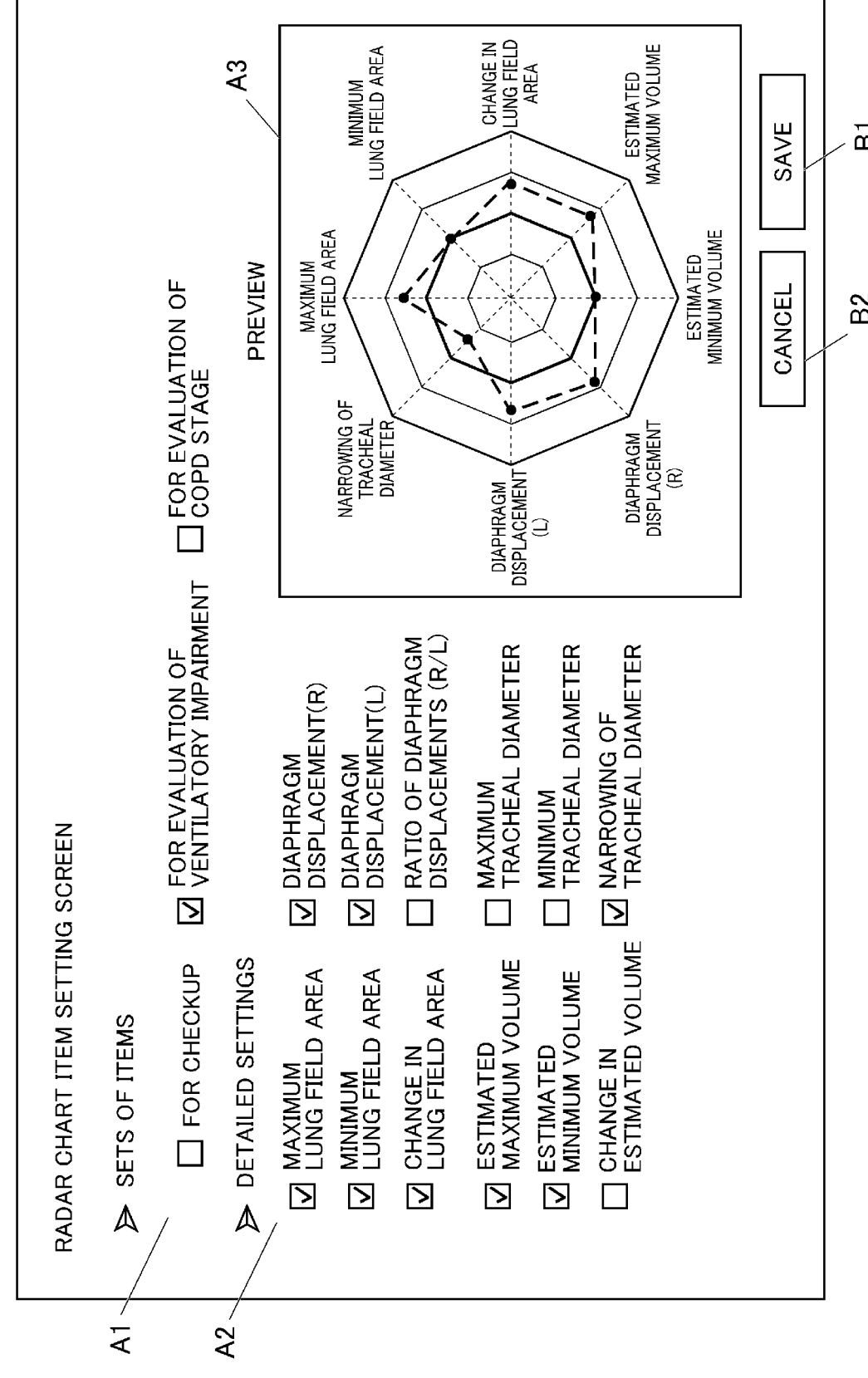
FIG. 4 shows an example of a radar chart item setting screen.

Next, the radiographer selects and confirms evaluation items (radar chart items, feature amounts or parameters) using a radar chart item setting screen shown in FIG. 4, and the controller 31 receives the selection results from the radiographer via the operation unit 33 (Step S17).

Hereinafter, the radar chart item setting screen shown in FIG. 4 will be described.

A sets-of-items section A1 is a section to select a set of evaluation items from among sets thereof stored in advance in the storage 32.

A detailed settings section A2 is a section to select evaluation items to be displayed on a radar chart preview image A3.

In accordance with a set checked (check-marked) in the sets-of-items section A1, evaluation items in the detailed settings section A2 are check-marked. More specifically, for example, when "For Evaluation of Ventilatory Impairment" is check-marked in the sets-of-items section A1, eight evaluation items in the detailed settings section A2 are check-marked, the eight evaluation items including "Maximum Lung Field Area" and "Minimum Lung Field Area".

The preview image A3 is a preview image of a radar chart generated on the basis of the evaluation items selected in the detailed settings section A2. This allows the radiographer to check a radar chart before it is finally output as a report.

A bold line therein indicates reference values of normal cases. On the radar chart, the reference values of the normal cases are "1".

A dashed line therein indicates relative values of the examinee (patient) to the reference values of the normal cases.

A save button B1 is a button to save the settings of the evaluation items. When the save button B1 is pressed, a radar chart is generated.

A cancel button B2 is a button to cancel the settings of the evaluation items. When the cancel button B2 is pressed, the report creation process is aborted.

Evaluation items in the detailed settings section A2 can be selected directly without using the sets-of-items section A1.

Order of the evaluation items on the preview image A3 can be changed by the radiographer dragging and dropping the evaluation item(s) on the preview image A3 using the mouse of the operation unit 33.

If there is no intention to change the selected/set evaluation items each time the report creation process is performed, a setting file in which the evaluation items are set may be stored in the storage 32 in advance. This can save time and effort to set evaluation items on the radar chart item setting screen each time the report creation process is performed.

In Step S18, the controller 31 sets the selection results as evaluation items (Step S18).

Next, the controller 31 generates a radar chart on the basis of the evaluation items set in Step S17 (Step S19).

Next, the controller 31 causes the display 34 to display a report including the radar chart (Step S20). For example, the display 34 displays a measurement result display screen (measurement result summary or report) shown in FIG. 5.

Hereinafter, the measurement result (report) display screen shown in FIG. 5 will be described.

In an area A4, the patient information, the examination information and so forth are displayed.

In an area A5, examination results are displayed. In the example shown in FIG. 5, change in the area of the lung fields ("Change in Lung Field Area"), change in the diameter of the trachea ("Change in Tracheal Diameter"), displacement of the diaphragm ("Diaphragm Displacement") and the lateral area of the lung fields ("Lateral Lung Field Area") are displayed.

For example, of the area A5, in a sub-area for the "Change in Lung Field Area", the reporting images selected in Step S16 are used, and the lung fields are enclosed by frames a so that their positions can be checked. At the upper right of the reporting images, the ratio of change in the area of the lung fields of the patient and the mean and the normal distribution of ratios of change in the area of the lung fields of healthy people, which are described below, are displayed. The normal distribution is displayed in gradations of color. At the lower right of the reporting images, a graph is displayed. The graph shows temporal change in the ratio of change in the area of the lung fields of the patient, and also shows the mean and the normal distribution of the ratios of change in the area of the lung fields of healthy people, with the horizontal axis representing examination dates (in the form of "Year/Month") of the patient.

In sub-areas for the "Change in Tracheal Diameter", the "Diaphragm Displacement" and the "Lateral Lung Field Area", details are displayed in the same manner.

In an area A6, a radar chart of the evaluation items set in Step S18 is displayed. As in FIG. 4, a bold line therein indicates the reference values of the normal cases, and a dashed line therein indicates the relative values of the examinee (patient) to the reference values of the normal cases.

When a report is thus created, the controller 31 outputs the report to an image storage apparatus, such as a PACS (Picture Archiving and Communication System), via the communication network NT. A doctor(s) can make a diagnosis on the basis of the report.

<Other Embodiments>

Figure 5:
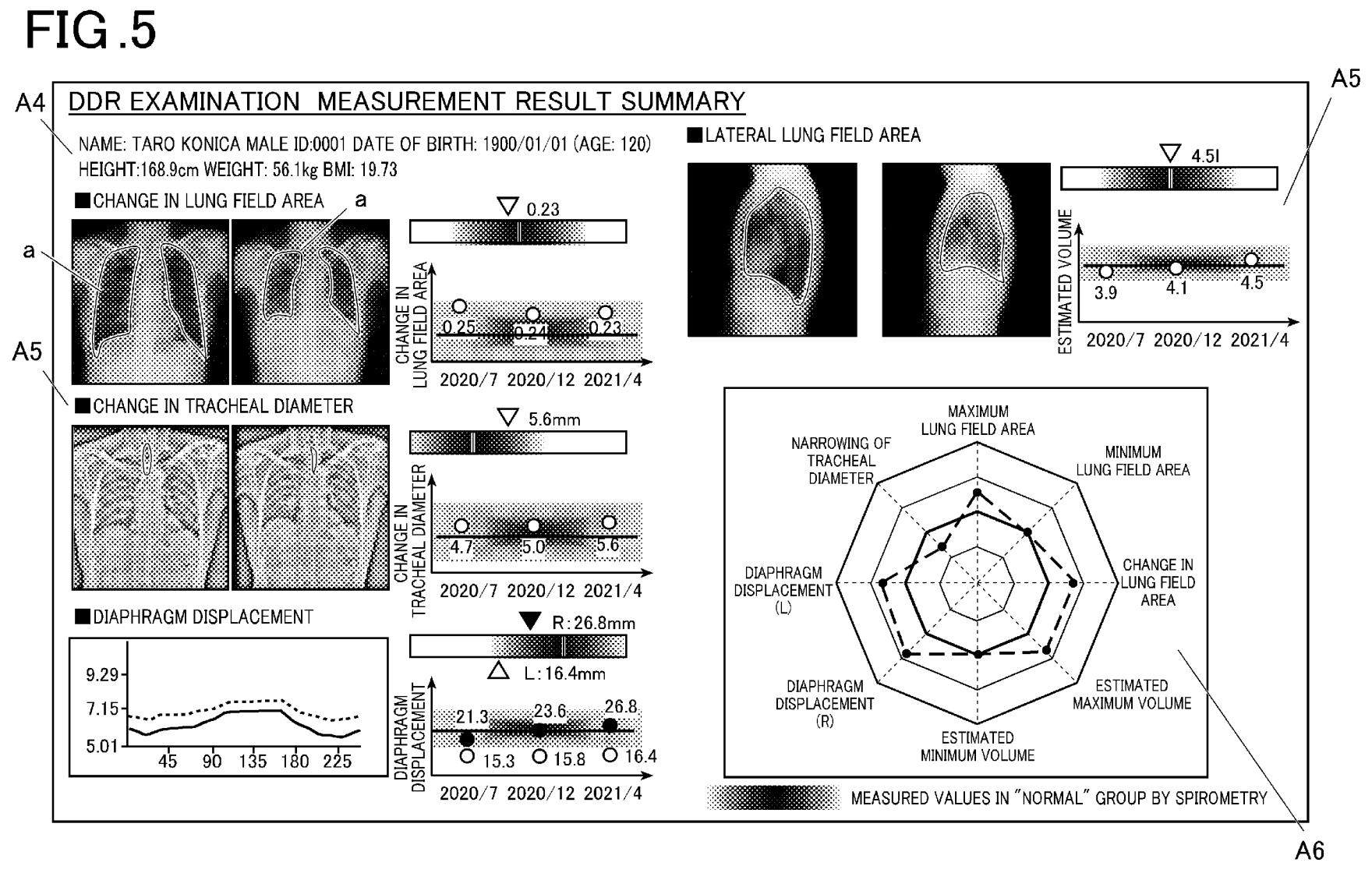
Figure 6:
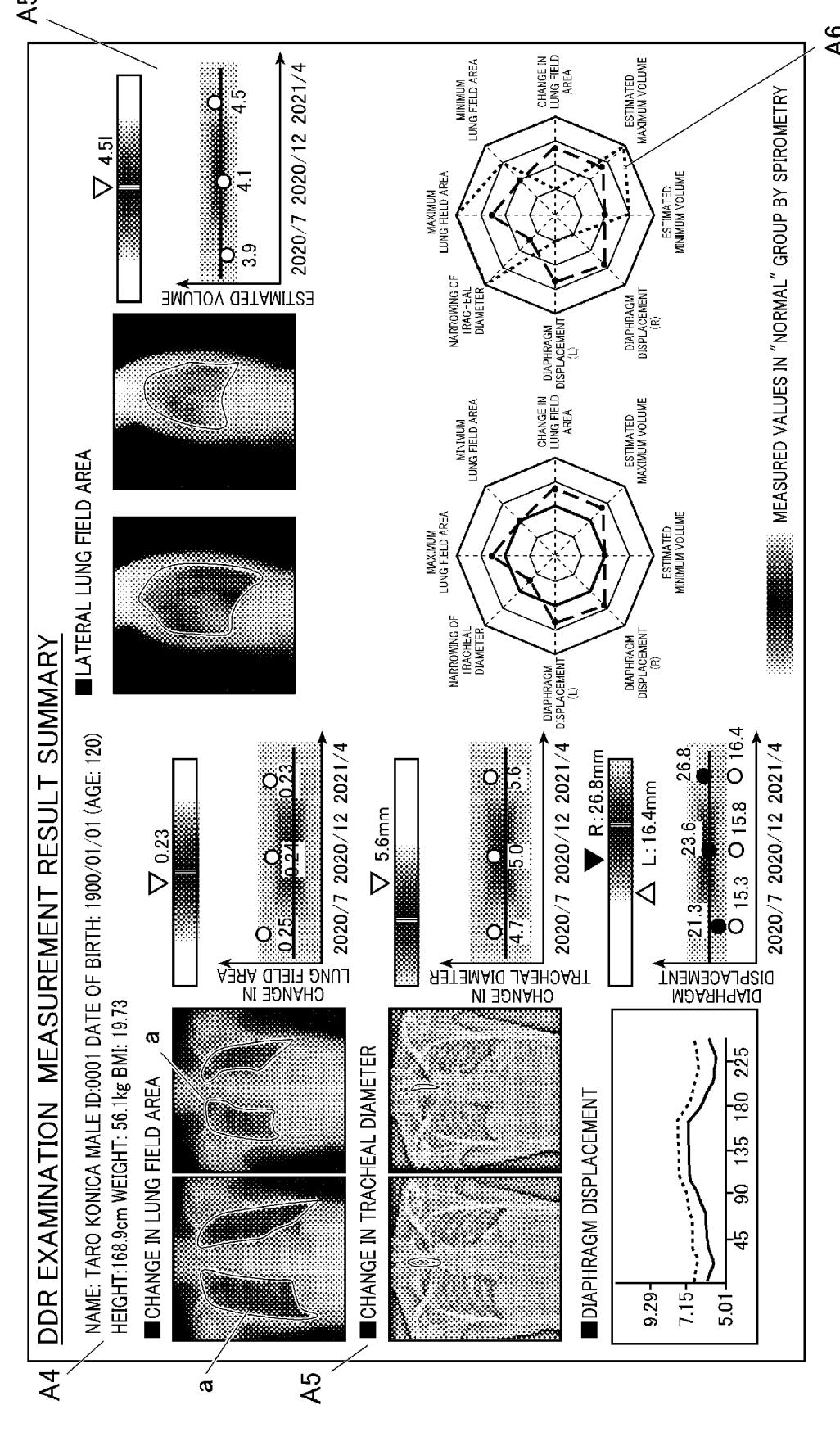
FIG. 6 shows an example of the measurement result display screen.

In the above embodiment, as shown in the measurement result display screen shown in FIG. 5, only one radar chart is displayed, but, for example, as shown in the measurement result display screen shown in FIG. 6, a plurality of radar charts may be displayed. In FIG. 6, a radar chart of the patient and the normal cases (reference values indicated by a bold line) and a radar chart of the patient and an obstructive pattern (indicated by a bold dotted line) are displayed side by side in the area A6. This makes it possible to compare the patient with the normal cases (reference values) and with the obstructive pattern at the same time. A plurality of radar charts in the area A6 may not be displayed side by side, but may be displayed in other forms, for example, one above another.

Figure 7:
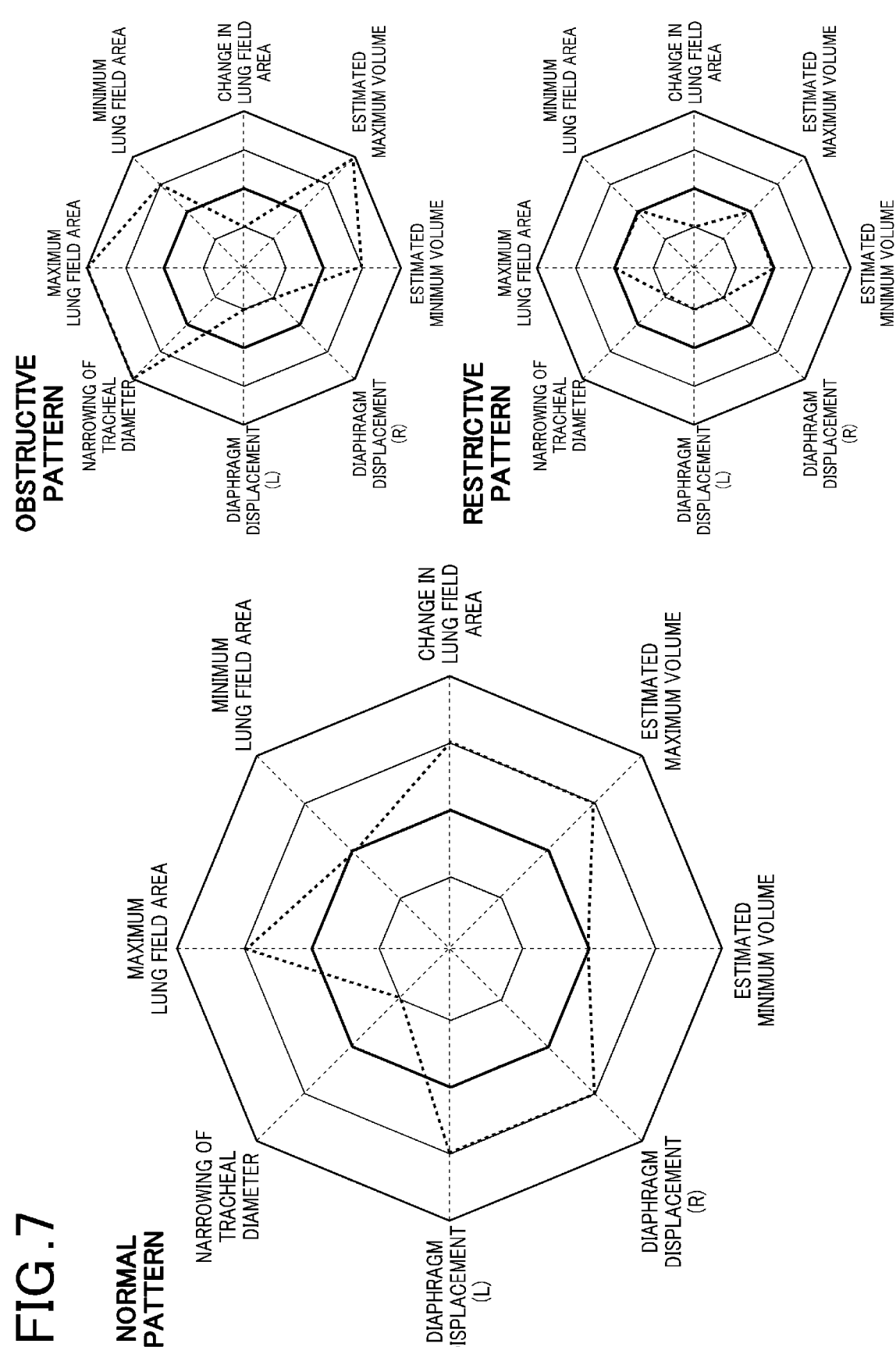
FIG. 7 shows examples of patterns of radar charts.

FIG. 7 shows examples of patterns, namely, a normal pattern, an obstructive pattern and a restrictive pattern, as indicated by bold dotted lines. More specifically, for example, in the case of a person(s) in a normal state of health in the disease ("healthy people" mentioned above), the values of the "Maximum Lung Field Area", the "Change In Lung Field Area", the "Estimated Maximum Volume" and the "Diaphragm Displacement" tend to be greater than their reference values, whereas the value of the "Narrowing of Tracheal Diameter" tends to be less than its reference value.

As in the above, bold lines therein indicate the reference values of the normal cases, which are "1".

Figure 8:
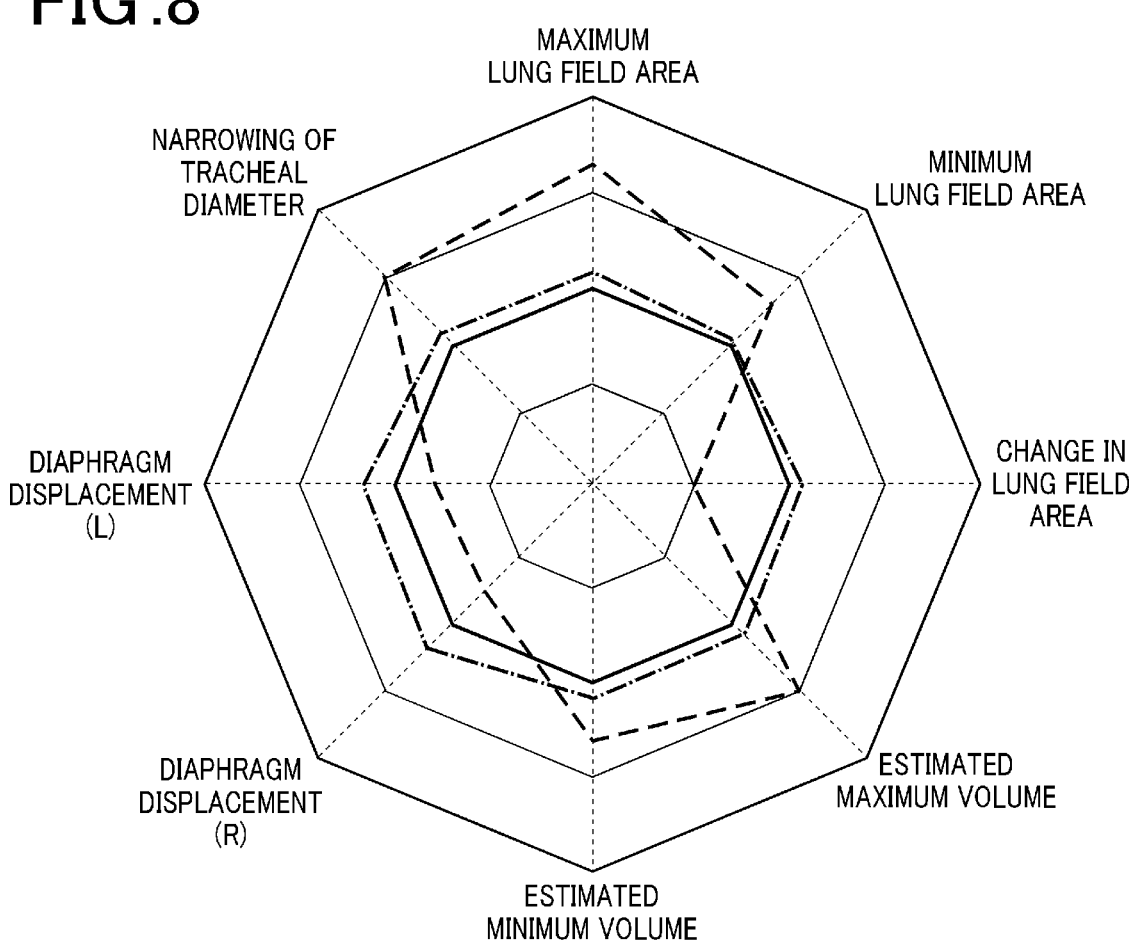
FIG. 8 shows a display example of a radar chart.

As shown in FIG. 8, a plurality of data (sets of values of evaluation items) may be displayed on a single radar chart. For example, FIG. 8 shows an example of a COPD (Chronic Obstructive Pulmonary Disease) patient treated and improved. In the case of COPD patients, the area of the lung fields tends to be large due to lung overexpansion, change in the area of the lung fields tends to be small because lungs hardly move due to lung overexpansion, the estimated volume tends to be large in accordance with the area, displacement of the diaphragm tends to be small due to lung overexpansion, and the trachea tends to narrow due to pressure change in the body caused by the disease. In FIG. 8, follow-up data of a diagnosis date of Jan. 28, 2021 ("2021/01/28" indicated by a dashed line) and follow-up data of a diagnosis date of Apr. 30, 2021 ("2021/04/30" indicated by a dashed-dotted line) of the patient can be compared with the reference values of the normal cases (indicated by a bold line) on the same radar chart, so that improvement of the COPD can be more clearly and easily seen.

Figure 9:
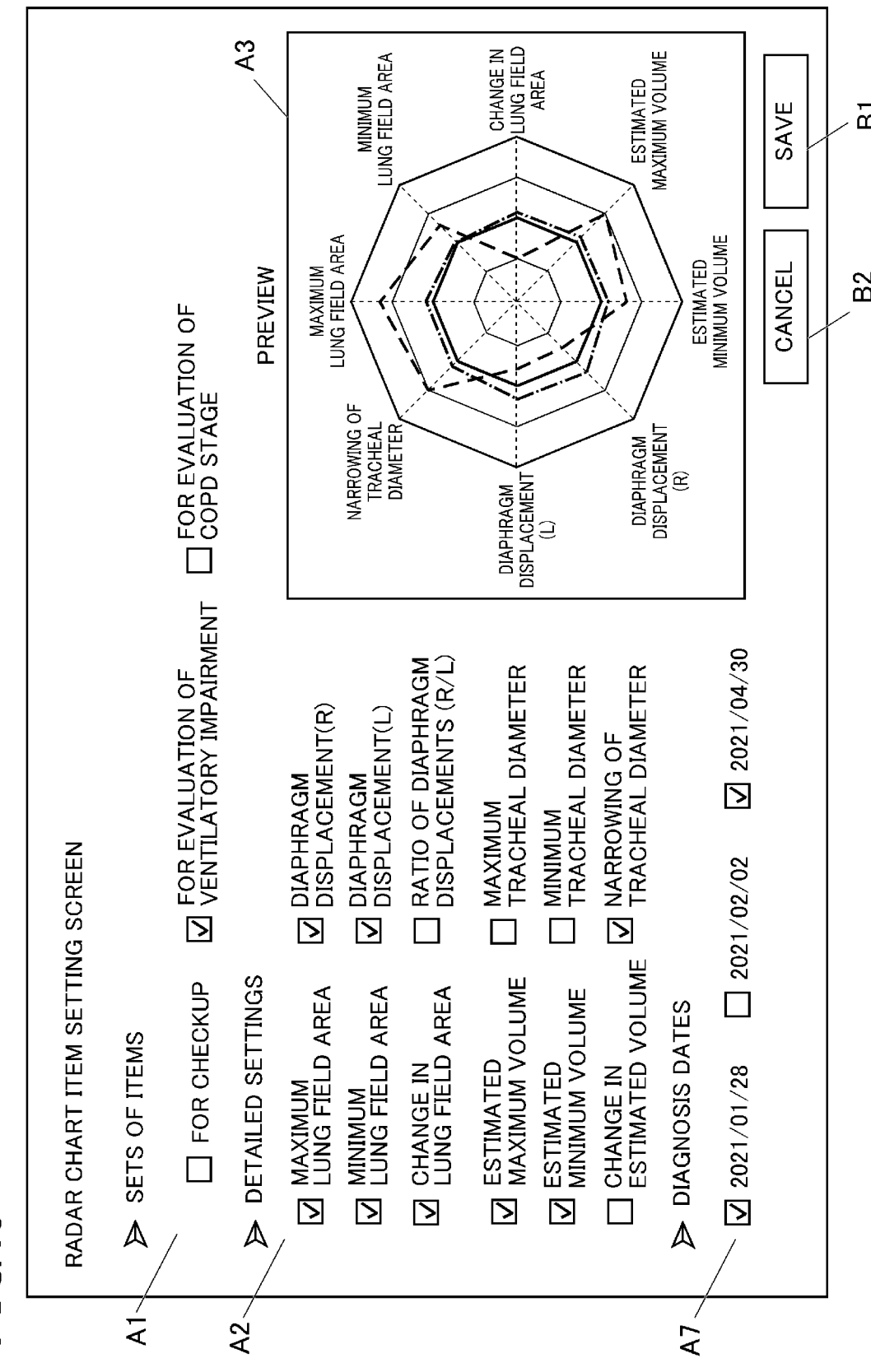
FIG. 9 shows an example of the radar chart item setting screen.

Further, for example, as shown in FIG. 9, a diagnosis dates section A7 is provided, and if there is a plurality of data (diagnosis dates of Jan. 28, 2021 ("2021/01/28"), Feb. 2, 2021 ("2021/02/02") and Apr. 30, 2021 ("2021/04/30") linked with the order information, the diagnosis dates section A7 is displayed so that the diagnosis dates are displayed, and on the basis of selected diagnosis dates (diagnosis dates of Jan. 28, 2021 and Apr. 30, 2021), data are displayed on a single radar chart so as to be superimposed on top of one another as shown in FIG. 8. If there is no plurality of data linked with the order information, the diagnosis dates section A7 may not be displayed.

Further, in Step S17, the radiographer may select one or more radar charts from among a plurality of radar charts. That is, a plurality of preview images of radar charts is displayed on the display 34, and the radiographer selects, using the operation unit 33, one or more radar charts to display in a report, instead of selecting evaluation items as in the above embodiment.

Further, a setting may be made such that the radiographer can change evaluation items as appropriate after selecting a radar chart(s).

Further, the color(s) of the evaluation items of a radar chart can be changed. For example, the color of letters and the color of a dotted line(s) of an evaluation item(s) on a radar chart can be changed to indicate that the evaluation item is an item to be noted, or that the value of the evaluation item has significantly changed from the one obtained at the previous examination. Such an evaluation item(s) of a radar chart may be provided with a mark, such as an asterisk.

Further, the evaluation items of a radar chart may be rearranged. For example, arrangement of the evaluation items may be changed such that evaluation items relevant to one another are arranged next to one another or in accordance with their large-small relationship. The controller 31 may automatically determine the relevance of the evaluation items of a radar chart, and display evaluation items highly relevant to one another next to one another.

Further, if examinations are performed first time (first examination) with an image analysis program Ver1.0 and second time (second examination) with an image analysis program Ver2.0 shown in FIG. 10, on a radar chart displayed at the second examination, there is no measurement result of the "Narrowing of Tracheal Diameter" at the first examination. In such a case, the image at the first examination may be obtained at the time of the second examination by Q/R (Query & Retrieve) from the image storage apparatus, and analyzed about the "Narrowing of Tracheal Diameter", so that the result can be displayed on the radar chart.

Further, the controller 31 may automatically select evaluation items of a radar chart on the basis of the order information.

For example, in Step S17 shown in FIG. 3, the controller 31 may cause the display 34 to display, from the beginning, the radar chart item setting screen shown in FIG. 4 where evaluation items are already selected in the sets-of-items section A1 and/or the detailed settings section A2 on the basis of the patient information, the examination information and so forth associated with the image obtained by the controller 31 in Step S11.

As another example, the controller 31 may automatically set radar chart items (evaluation items) on the basis of the patient information, the examination information and so forth associated with the image obtained by the controller 31 in Step S11, and generate a radar chart in Step S19, skipping Steps S17 and S18, namely, without displaying the radar chart item setting screen.

For the automatic selection, association of patient information, examination information and so forth with radar chart items is preset on the basis of knowledge obtained from diagnoses in the past or the like.

Further, the controller 31 may cause the display 34 to prominently display a primary evaluation item(s) among a plurality of evaluation items, for example, in boldface type, in the radar chart item setting screen shown in FIG. 4.

Further, in the above, the lung field regions are the analysis region, but another organ may be the analysis target, namely, the analysis region.

More specifically, as shown in FIG. 11, a heart ROI (Region of Interest) may be the analysis region, and change in signal value (signal value change) (S_Inhalation/S_Exhalation) calculated from the mean signal value of the heart ROI at the time of inhalation (S_Inhalation) (left in FIG. 11) and the mean signal value thereof at the time of exhalation (S_Exhalation) (right in FIG. 11) may be used as an evaluation item.

Further, in the above, a dynamic image is used, but a still image may be used. In this case, the imaging apparatus 1 functions as an imager that takes still images.

Figure 12:
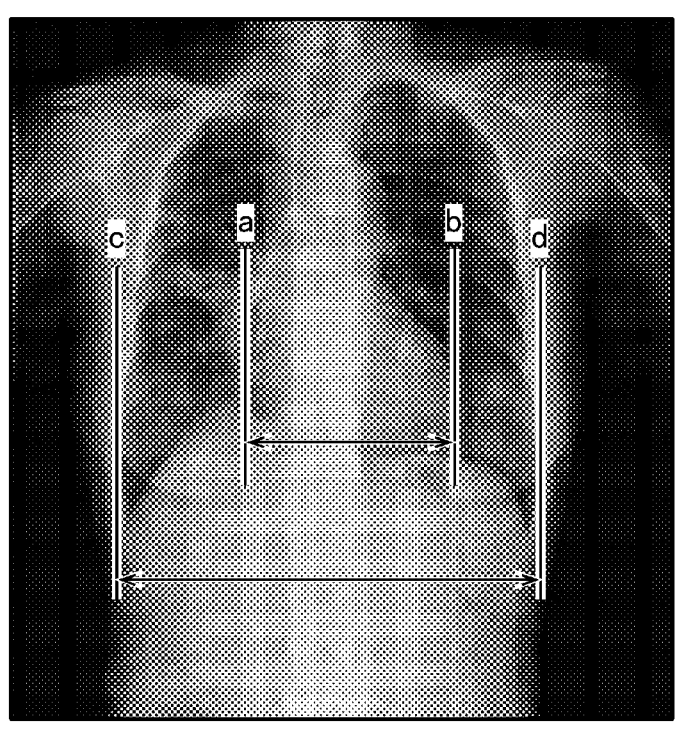
FIG. 12 shows an example of a still image.

More specifically, a still image as shown in FIG. 12 is used, and the ratio of the heart to the thorax (cardiothoracic ratio) is observed as an evaluation item. In the example shown in FIG. 12, the cardiothoracic ratio is expressed by "(b−a)/(d−c)×100".

Further, in the above, the medical image is a dynamic image obtained by radiographing, but not limited thereto. For example, the medical image may be an ultrasound image(s).

Figure 13:
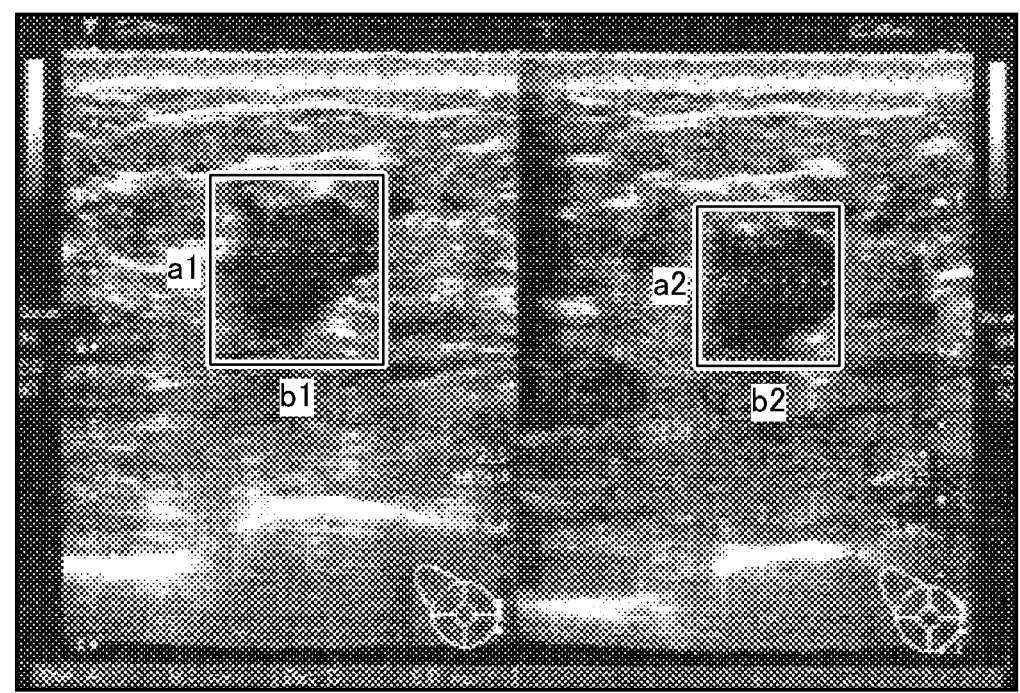
FIG. 13 shows examples of ultrasound images.

More specifically, the medical image may be ultrasound images as shown in FIG. 13, and change in shape of an examination target site may be observed as an evaluation item using D/W ratio (a1/b1 and a2/b2) at a dynamic test (examination to see change in shape by pressing a probe to an examination target site).

<Effects, Etc>

As described above, the image processing apparatus (diagnostic console 3) includes the controller 31 that obtains a medical image in which a subject is imaged, the medical image being obtained by examining the subject, to be more specific, obtained by imaging the subject with radiation, calculates a value(s) of an evaluation item(s) based on the medical image, sets evaluation items among a plurality of evaluation items, generates a radar chart using the value of each of the set evaluation items, and outputs the radar chart. This makes it possible to generate a suitable radar chart(s) in accordance with a disease and an observation site about which analysis is performed.

Further, the medical image is a dynamic image. This increases the number of analyzable evaluation items as compared with a still image, and makes it possible to generate a more suitable radar chart(s) for diagnosis.

Further, the controller 31 calculates, as the value of the evaluation item, a value of time-series information based on the dynamic image. Hence, time-series information can be used for a radar chart.

Further, the time-series information as the evaluation item includes an evaluation item related to a motion of an organ and an evaluation item related to a signal value change accompanying the motion of the organ. Examples of the time-series information (evaluation items) include the maximum area of lung fields, the minimum area of lung fields, (ratio of) change in the area of lung fields, estimated maximum volume, estimated minimum volume, displacement of right diaphragm, displacement of left diaphragm, (amount of) narrowing of tracheal diameter, and change in signal value (signal value change) of a heart ROI.

Further, the controller 31 generates the radar chart provided with reference values of a normal case(s) for the respective set evaluation items. This allows the user to see and compare data of a patient with data of healthy people.

Further, the controller 31 generates, as the radar chart, a plurality of radar charts. This allows the user to see and compare radar charts with one another on a screen.

Further, the image processing apparatus (diagnostic console 3) further includes the operation receiver (operation unit 33) that receives a user operation(s) to select one or more radar charts from the plurality of radar charts, and the controller 31 outputs the selected one or more radar charts. This makes it smooth to select a radar chart(s) because the user does not need to select evaluation items one by one to generate a radar chart(s), but can select a radar chart(s) on the basis of preview images of radar charts.

Further, the controller 31 outputs the plurality of radar charts. This allows the user to see and compare radar charts with one another on a screen.

Further, the controller 31 sets the evaluation items based on the order information. For this, knowledge obtained from diagnoses in the past or the like can be utilized, and the user can check the initially displayed screen where evaluation items are already selected, and after checking the evaluation items recommended for diagnosis, reselect an evaluation item(s) or fix the selected evaluation items as they are. The above also reduces time and effort to select evaluation items. If a setting is made to automatically generate a radar chart using the evaluation items automatically selected on the basis of the order information, it further reduces time and effort.

Further, the image processing apparatus (diagnostic console 3) includes the operation receiver (operation unit 33) that receives a user operation(s) to set the evaluation items, and the controller 31 sets the evaluation items corresponding to the user operation(s) received by the operation unit 33. This makes it possible to precisely select evaluation items as requested by the user.

Further, the number of the evaluation items to be set by the controller 31 is variable. This makes it possible to change parameters of a radar chart in accordance with a disease and an observation site about which analysis is performed.

The image processing system 100 includes the controller 31 that obtains a medical image obtained by imaging a subject with radiation, calculates a value(s) of an evaluation item(s) based on the medical image, sets evaluation items among a plurality of evaluation items, generates a radar chart using the value of each of the set evaluation items, and outputs the radar chart. This makes it possible to generate a suitable radar chart(s) in accordance with a disease and an observation site about which analysis is performed.

The non-transitory computer-readable storage medium stores the program that causes the computer (controller 31) of the image processing apparatus (diagnostic console 3) to obtain a medical image obtained by imaging a subject with radiation, calculate a value(s) of an evaluation item(s) based on the medical image, set evaluation items among a plurality of evaluation items, generate a radar chart using the value of each of the set evaluation items, and output the radar chart. This makes it possible to generate a suitable radar chart(s) in accordance with a disease and an observation site about which analysis is performed.

Those described in the above embodiments are some of preferred examples of the present disclosure, and hence the present disclosure is not limited thereto.

For example, in the above embodiments, the controller 31 uses a single medical image (dynamic image) to generate a radar chart(s), but may use multiple types of medical images (dynamic image, still image, etc.) to generate a radar chart(s).

Further, in the above, the computer-readable storage medium storing the program(s) of the present disclosure is a hard disk, a nonvolatile semiconductor memory or the like, but not limited thereto and may be a portable recording medium, such as a CD-ROM. Further, as a medium to provide data of the program(s) of the present disclosure via a communication line, a carrier wave can be used.

The other detailed configurations/components and operations of the apparatuses of the image processing system can also be appropriately changed without departing from the scope of the present disclosure.

Although some embodiments of the present disclosure have been described and illustrated in detail, the disclosed embodiments are made for purposes of not limitation but illustration and example only. The scope of the present disclosure should be interpreted by terms of the appended claims.

The invention claimed is:

1. An image processing apparatus comprising a hardware processor that obtains a medical image in which a subject is imaged, the medical image being a dynamic image, sets evaluation items among a plurality of evaluation items, outputs an indication of at least one of the set evaluation items with the mean and normal distribution of the at least one of the set evaluation items of healthy people, generates a radar chart using a calculated value of each of the set evaluation items based on the dynamic image, and outputs the radar chart, wherein the radar chart shows:

the calculated value of the each of the set evaluation items, and one or both of reference values of a normal case and reference values of an abnormal condition case.

2. The image processing apparatus according to claim 1, wherein the hardware processor calculates, as the value of the evaluation item, a value of time-series information based on the dynamic image.

3. The image processing apparatus according to claim 2, wherein the time-series information as the evaluation item includes an evaluation item related to a motion of an organ and an evaluation item related to a signal value change accompanying the motion of the organ.

4. The image processing apparatus according to claim 1, wherein the hardware processor generates the radar chart provided with the reference values of the normal case for the respective set evaluation items.

5. The image processing apparatus according to claim 1, wherein the hardware processor generates, as the radar chart, a plurality of radar charts.

6. The image processing apparatus according to claim 5, further comprising an operation receiver that receives a user operation to select one or more radar charts from the plurality of radar charts, wherein the hardware processor outputs the selected one or more radar charts.

7. The image processing apparatus according to claim 5, wherein the hardware processor outputs the plurality of radar charts.

8. The image processing apparatus according to claim 5, wherein the plurality of radar charts includes a first radar chart showing the calculated value of the each of the set evaluation items and the reference values of the normal case and a second radar chart showing the calculated value of the set evaluation items and the reference values of the abnormal condition.

9. The image processing apparatus according to claim 8, wherein the hardware processor outputs the plurality of radar charts or outputs a user selected one or more of the plurality of radar charts.

10. The image processing apparatus according to claim 1, wherein the hardware processor sets the evaluation items based on order information.

11. The image processing apparatus according to claim 1, further comprising an operation receiver that receives a user operation to set the evaluation items, wherein the hardware processor sets the evaluation items corresponding to the user operation received by the operation receiver.

12. The image processing apparatus according to claim 1, wherein the number of the evaluation items to be set by the hardware processor is variable.

13. The image processing apparatus according to claim 1, wherein the hardware processor calculates, as a value of one of the evaluation items, a value of time-series information based on the dynamic image, and the time-series information is related to a change in a signal value of pixels in a region of interest accompanying the motion of the organ in the dynamic image.

14. The image processing apparatus according to claim 1, wherein the indication of the normal distribution is displayed in gradations of color.

15. An image processing system comprising:

an examination apparatus that obtains a medical image in which a subject is imaged;

an image processing apparatus that is connected to the examination apparatus; and a hardware processor that obtains the medical image from the examination apparatus, the medical image being a dynamic image,

sets evaluation items among a plurality of evaluation
items,
outputs an indication of at least one of the set evalua-
tion items with the mean and normal distribution of
the at least one of the set evaluation items of healthy
people,
generates a radar chart using a calculated value of each
of the set evaluation items based on the dynamic
image, and
outputs the radar chart,
wherein the radar chart shows:
the calculated value of the each of the set evaluation
items, and
one or both of reference values of a normal case and
reference values of an abnormal condition case.
   16. A non-transitory computer-readable storage medium
storing a program that causes a computer of an image
processing apparatus to:

16 obtain a medical image in which a subject is imaged, the
medical image being a dynamic image;
set evaluation items among a plurality of evaluation
items;
output an indication of at least one of the set evaluation
items with the mean and normal distribution of the at
least one of the set evaluation items of healthy people,
generate a radar chart using a calculated value of each of
the set evaluation items based on the dynamic image;
and
output the radar chart,
wherein the radar chart shows:
the calculated value of the each of the set evaluation
items, and
one or both of reference values of a normal case and
reference values of an abnormal condition case.

* * * * *